(12) United States Patent
Sandford et al.

(10) Patent No.: US 7,931,880 B2
(45) Date of Patent: Apr. 26, 2011

(54) PRODUCTION OF SILVER SULFATE GRAINS USING INORGANIC ADDITIVES

(75) Inventors: David W. Sandford, Rochester, NY (US); Thomas N. Blanton, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 1035 days.

(21) Appl. No.: 11/694,582

(22) Filed: Mar. 30, 2007

(65) Prior Publication Data

US 2008/0241511 A1 Oct. 2, 2008

(51) Int. Cl.
C01G 5/00 (2006.01)

(52) U.S. Cl. ............ 423/42; 423/45; 423/266; 423/275; 423/462; 423/544

(58) Field of Classification Search ...................... 423/42, 423/45, 266, 275, 462, 544
See application file for complete search history.

(56) References Cited

U.S. PATENT DOCUMENTS

| | | | |
|---|---|---|---|
| 4,525,410 A | 6/1985 | Hagiwara et al. | |
| 4,728,323 A | 3/1988 | Matson | |
| 5,049,140 A | 9/1991 | Brenner et al. | |
| 5,064,599 A | 11/1991 | Ando et al. | |
| 5,180,402 A | 1/1993 | Kubota et al. | |
| 5,496,860 A | 3/1996 | Matsumoto et al. | |
| 5,880,044 A | 3/1999 | Shimiz | |
| 5,888,526 A | 3/1999 | Tsubai et al. | |
| 6,248,342 B1 | 6/2001 | Trogolo et al. | |
| 6,274,519 B1 | 8/2001 | Omori et al. | |
| 6,436,420 B1 | 8/2002 | Antelman | |
| 6,479,144 B2 | 11/2002 | Petrea et al. | |
| 6,585,843 B2 | 7/2003 | Nickell et al. | |
| 7,261,867 B1 | 8/2007 | Sandford et al. | |

FOREIGN PATENT DOCUMENTS

| | | |
|---|---|---|
| GB | 1082653 | 9/1967 |
| JP | 03-271208 | 3/1991 |
| JP | 10197977 | 7/1998 |
| JP | 28-41115 B2 | 12/1998 |
| JP | 2005139292 | 2/2005 |
| JP | 2005330195 | 2/2005 |
| JP | 2005330195 A * | 12/2005 |
| WO | WO 2005/080488 | 9/2005 |
| WO | WO 2006/113052 | 10/2006 |

OTHER PUBLICATIONS

Theodore W. Richards et al; Z. anorg. Allg. Chem. 55; 72 (1907).
O. Honigschmid et al; Z. anorg. Allg. Chem. 195; 207 (1931).
Harry Hahn et al; Z. anorg. Allg. Chem. 258; 91 (1949).
J.A. Spadaro et al; *Clinical Orthopaedics and Related Research*; "Silver Polymethyl Methacrylate Antibacterial Bone Cement"; No. 143, pp. 266-270; 1979.
I.B. Romans; *Disinfection, Sterilization and Preservation*; "Oligodynamic Metals"; pp. 372-400, 1968.
A. Goetz et al; *Silver In Industry*; Chapter 16;"The Oligodynamic Effect of Silver"; pp. 401-429; (1940).
Stewart C. Harvey et al; *The Pharmacological Basis of Therapeutics*; Chapter 41; "Antiseptics and Disinfectants; Fungicides; Ectoparasiticides"; Sixth Ed.; 1980; pp. 964-987.
Stewart C. Harvey et al; *The Pharmacological Basis of Therapeutics*; Chapter 46; "Heavy Metals"; Fifth Ed.; 1975; pp. 924-945.

* cited by examiner

*Primary Examiner* — Kelechi C Egwim
(74) *Attorney, Agent, or Firm* — Andrew J. Anderson; J. Lanny Tucker

(57) ABSTRACT

An aqueous precipitation process for the preparation of particles comprising primarily silver sulfate, comprising reacting an aqueous soluble silver salt and an aqueous soluble source of inorganic sulfate ion in an agitated precipitation reactor vessel and precipitating particles comprising primarily silver sulfate, wherein the reaction and precipitation are performed in the presence of an aqueous soluble inorganic additive compound containing a cation capable of forming a sulfate salt that is less soluble than silver sulfate or a halide anion or an oxyanion capable of forming a silver salt that is less soluble than silver sulfate, the amount of additive being a minor molar percentage, relative to the molar amount of silver sulfate precipitated, and effective to result in precipitation of particles comprising primarily silver sulfate having a mean grain-size of less than 70 micrometers.

9 Claims, No Drawings

PRODUCTION OF SILVER SULFATE GRAINS USING INORGANIC ADDITIVES

CROSS REFERENCE TO RELATED APPLICATIONS

Reference is made to commonly assigned, concurrently-filed, copending U.S. Ser. No. 11/694,390 directed towards "Color Stabilized Antimicrobial Polymer Composites", the disclosure of which is incorporated by reference herein.

FIELD OF THE INVENTION

The present invention relates to the production of silver sulfate particles produced by aqueous precipitation methods, and in particular micron sized silver sulfate particles produced with uniform size employing inorganic additives, and the use thereof as an antimicrobial and antiviral agent in polymeric materials.

BACKGROUND OF THE INVENTION

There are various uses for silver sulfate, including as a synthetic reagent; a source of silver in the preparation of catalysts, plastic composite materials and various platinum complexes; as well as a source of silver in some photographic processes. Recently silver sulfate has been incorporated into plastics and facial creams as an antimicrobial and antifungal agent. To satisfy the demands of many modem applications, reduction of particle sizes of materials to the micron and nanometer size ranges is often required to take advantage of the higher surface area, surface energy, reactivity, dispersability and uniformity of these size particles; as well as the uniformity and smoothness of coatings made thereof, optical clarity due to reduced light scatter, etc., inherent in these forms of matter. In addition, with the miniaturization of the physical size of many objects and devices, a similar limitation on the physical size of material components is now commonly encountered.

Silver sulfate is a commercially available material that is produced by conventional aqueous precipitation methods. The reaction of equimolar amounts of aqueous solutions of silver nitrate and sulfuric acid to from silver sulfate was described by Th. W. Richards and G. Jones, *Z. anorg. Allg. Chem.* 55, 72 (1907). A similar precipitation process using sodium sulfate as the source of sulfate ion was reported by O. Honigschmid and R. Sachtleben, *Z. anorg. Allg. Chem.* 195, 207 (1931). An alternate method employing the immersion of silver metal in a sulfuric acid solution was also reported by O. Honigschmid and R. Sachtleben (loc. cit.). Precipitation of finely divided silver sulfate from an aqueous solution via the addition of alcohol was later reported by H. Hahn and E. Gilbert, *Z. anorg. Allg. Chem.* 258, 91 (1949). Silver salts are widely known to be thermally and photolytically unstable, discoloring to form brown, gray or black products. Silver ion may be reduced to its metallic state, or oxidized to silver oxide, or react with sulfur to form silver sulfide. Silver sulfate has been observed to decompose by light to a violet color.

The antimicrobial properties of silver have been known for several thousand years. The general pharmacological properties of silver are summarized in "Heavy Metals"—by Stewart C. Harvey and "Antiseptics and Disinfectants: Fungicides; Ectoparasiticides"—by Stewart Harvey in *The Pharmacological Basis of Therapeutics*, Fifth Edition, by Louis S. Goodman and Alfred Gilman (editors), published by MacMillan Publishing Company, NY, 1975. It is now understood that the affinity of silver ion to biologically important moieties such as sulfhydryl, amino, imidazole, carboxyl and phosphate groups are primarily responsible for its antimicrobial activity.

The attachment of silver ions to one of these reactive groups on a protein results in the precipitation and denaturation of the protein. The extent of the reaction is related to the concentration of silver ions. The diffusion of silver ion into mammalian tissues is self-regulated by its intrinsic preference for binding to proteins through the various biologically important moieties on the proteins, as well as precipitation by the chloride ions in the environment. Thus, the very affinity of silver ion to a large number of biologically important chemical moieties (an affinity which is responsible for its action as a germicidal/biocidal/ viricidal/fungicidal/bacteriocidal agent) is also responsible for limiting its systemic action—silver is not easily absorbed by the body. This is a primary reason for the tremendous interest in the use of silver containing species as an antimicrobial, i.e., an agent capable of destroying or inhibiting the growth of microorganisms, such as bacteria, yeast, fungi and algae, as well as viruses. In addition to the affinity of silver ions to biologically relevant species that leads to the denaturation and precipitation of proteins, some silver compounds, those having low ionization or dissolution ability, also function effectively as antiseptics. Distilled water in contact with metallic silver becomes antibacterial even though the dissolved concentration of silver ions is less than 100 ppb. There are numerous mechanistic pathways by which this oligodynamic effect is manifested, i.e., ways in which silver ion interferes with the basic metabolic activities of bacteria at the cellular level to provide a bactericidal and/or bacteriostatic effect.

A detailed review of the oligodynamic effect of silver can be found in "Oligodynamic Metals" by I. B. Romans in *Disinfection, Sterilization and Preservation*, C. A. Lawrence and S. S. Bloek (editors), published by Lea and Fibiger (1968) and "The Oligodynamic Effect of Silver" by A. Goetz, R. L. Tracy and F. S. Harris, Jr. in *Silver in Industry*, Lawrence Addicks (editor), published by Reinhold Publishing Corporation, 1940. These reviews describe results that demonstrate that silver is effective as an antimicrobial agent towards a wide range of bacteria, and that silver can impact a cell through multiple biochemical pathways, making it difficult for a cell to develop resistance to silver. However, it is also known that the efficacy of silver as an antimicrobial agent depends critically on the chemical and physical identity of the silver source. The silver source can be silver in the form of metal particles of varying sizes, silver as a sparingly soluble material such as silver chloride, silver as a moderately soluble salt such as silver sulfate, silver as a highly soluble salt such as silver nitrate, etc. The efficiency of the silver also depends on i) the molecular identity of the active species—whether it is $Ag^+$ ion or a complex species such as $(AgSO_4)^-$, etc., and ii) the mechanism by which the active silver species interacts with the organism, which depends on the type of organism. Mechanisms can include, for example, adsorption to the cell wall which causes tearing; plasmolysis where the silver species penetrates the plasma membrane and binds to it; adsorption followed by the coagulation of the protoplasm; or precipitation of the protoplasmic albumin of the bacterial cell. The antibacterial efficacy of silver is determined, among other factors, by the nature and concentration of the active species, the type of bacteria; the surface area of the bacteria that is available for interaction with the active species, the bacterial concentration, the concentration and/or the surface area of species that could consume the active species and lower its activity, and the mechanisms of deactivation.

One proposed use of silver based antimicrobials is for textiles. Various methods are known in the art to render antimicrobial properties to a target fiber. The approach of embedding inorganic antimicrobial agents, such as zeolites, into low melting components of a conjugated fiber is described in U.S. Pat. Nos. 4,525,410, and 5,064,599. In another approach, the antimicrobial agent can be delivered during the process of making a synthetic fiber such as those described in U.S. Pat. Nos. 5,180,402, 5,880,044, and 5,888,526, or via a melt extrusion process as described in U.S. Pat. Nos. 6,479,144 and 6,585,843. In still yet another process, an antimicrobial metal ion can be ion exchanged with an ion exchange fiber as described in U.S. Pat. No. 5,496,860.

High-pressure laminates containing antimicrobial inorganic metal compounds are disclosed in U.S. Pat. No. 6,248,342. Deposition of antimicrobial metals or metal-containing compounds onto a resin film or target fiber has also been described in U.S. Pat. Nos. 6,274,519 and 6,436,420.

In particular, the prior art has disclosed formulations that are useful for highly soluble silver salts having aqueous solubility products, herein referred to as pKsp, of less than 1. In general, these silver salts require the use of hydrophobic addenda to provide the desired combination of antimicrobial behavior and durability. Conversely, it is also known that very insoluble metallic silver particles, having a pKsp greater than 15, would require hydrophilic addenda to provide the desired combination of antimicrobial behavior and durability. There exists a need to provide sparingly soluble silver salts in the range of pKsp from about 3-8, which can be highly efficient in antimicrobial and antiviral behavior when incorporated directly into plastics and polymeric materials.

The use of an organo-sulfate or organo-sulfonate additive as a means of controlling the particle size of precipitated silver sulfate is disclosed in U.S. Pat. No. 7,261,867. However, the inclusion of substantial amounts of organic character in additives to silver sulfate materials has been shown to compromise the thermal stability. For example, when compounded into melt-processed polymers such as polypropylene, an unacceptable degree of discoloration of the composites often results.

Parasiticidal preparations of metal alkylsulphates and metal detergent sulphonates are described by Duperray in GB 1,082,653. Disclosures include the preparation of silver salts of alkylsulphates (specifically, silver laurylsulfphate and silver lauroylamino-ethylsulphate) and the silver salt of an alkylarylsulphonate (specifically, silver dodecylbenzenesulphonate). These compounds are prepared by reacting an excess of the alkylsulphate or alkylarylsulphonate with silver hydroxide, to form a neutral salt (or 1:1 adduct). While considerable efficacy in destroying parasitic protozoa such as coccidiae and histomones resulted when these compounds were added to the drinking water of diseased chickens, turkeys and cattle, neutral silver salts of these kinds contain too much organic character for use in some applications. Specifically, silver laurylsulphate has been observed to be extremely discolored when added into even a relatively low temperature (about 170° C.) melt of a polyolefin. This result is typical of polymer melt additives that either contain too much unstable organic character or are simply added in an excessive amount.

An antimicrobial masterbatch formulation is disclosed in JP 2841115B2 wherein a silver salt and an organic antifungal agent are combined in a low melting wax to form a masterbatch with improved dispersibility and handling safety. More specifically, silver sulfate was sieved through a 100 mesh screen (particles sizes less than about 149 microns), combined with 2-(4-thiazolyl)benzimidazole and kneaded into polyethylene wax. This masterbatch material was then compounded into polypropylene, which was subsequently injection molded into thin test blocks. These test blocks were reported to be acceptable for coloration and thermal stability, while exhibiting antibacterial properties with respect to *E. coli* and *Staphylococcus*, and antifungal properties with respect to *Aspergillus niger*. Similar masterbatches are also described in JP 03271208, wherein a resin discoloration-preventing agent (e.g. UV light absorbent, UV light stabilizer, antioxidant) is also incorporated.

An antimicrobial mixture of zinc oxide and silver sulfate on an inorganic powder support is disclosed in JP 08133918, wherein the inorganic powder support is selected from calcium phosphate, silica gel, barium sulfate and titanium oxide. The average primary particle diameter of the inorganic carrier powder is preferably $\leq$10 microns, more preferably $\leq$5 microns. The amount of silver sulfate supported is $\geq$0.04% and <5.0%, especially preferably $\geq$0.3% and <1.8%. The ratio of zinc oxide to the inorganic powder supporting silver sulfate is selected from the range of 0.2:99.8 to 30:70. The low overall content of antimicrobially active silver sulfate (<5.0%) in these particulate mixtures requires a relatively high loading of the mixture into a polymer or other substrate.

Silver sulfate has been proposed as an antimicrobial agent in a number of medical applications. Incorporation of inorganic silver compounds in bone cement to reduce the risk of post-operative infection following the insertion of endoprosthetic orthopaedic implants was proposed and studied by J. A. Spadaro et al (Clinical Orthopaedics and Related Research, 143, 266-270, 1979). Silver chloride, silver oxide, silver sulphate and silver phosphate were incorporated in polymethylmethacrylate bone cement at 0.5% concentration and shown to significantly inhibit the bacterial growth of *Staphylococcus aureus, Escherichia coli* and *Pseudomonas aeruginosa*. Antimicrobial wound dressings are disclosed in U.S. Pat. No. 4,728,323; wherein a substrate is vapor or sputter coated with an antimicrobially effective film of a silver salt, preferably silver chloride or silver sulfate. Antimicrobial wound dressings are disclosed in WO2006113052A2; wherein aqueous silver sulfate solutions are dried onto a substrate under controlled conditions to an initial color, which is color stable for preferably one week under ambient light and humidity conditions. An antimicrobial fitting for a catheter is disclosed in U.S. Pat. No. 5,049,140; wherein a proposal to fabricate a tubular member composed of a silicone/polyurethane elastomer in which is uniformly dispersed about 1 to 15% wt. of an antimicrobial agent, preferably silver sulfate, is described. A moldable plastic composite comprising cellulose and a urea/formaldehyde resin is disclosed in WO2005080488A1, wherein a silver salt, specifically silver sulfate, is incorporated to provide a surface having antiviral activity against SARS (severe acute respiratory syndrome) coronavirus.

Despite various references to the proposed use of silver salts as antimicrobial agents in various fields as referenced above, there are limited descriptions with respect to approaches in the prior art for preparing silver salts, specifically silver sulfate, of sufficiently small grain-size and of optimal grain-size distribution as may be desired for particular applications. A need exists, in particular, to provide antimicrobial agents such as silver salts, more specifically silver sulfate, in controlled particular sizes for use in plastics and polymer containing materials with improved antimicrobial efficacy and reduced cost, while avoiding discoloration and enabling more robust manufacturing processes. A process of preparing silver sulfate with improved thermal stability that is simple, cost effective, and contains less organic material as an additive is desired.

SUMMARY OF THE INVENTION

In accordance with one embodiment, the present invention is directed towards a process comprising reacting an aqueous soluble silver salt and an aqueous soluble source of inorganic sulfate ion in an agitated precipitation reactor vessel and precipitating particles comprising primarily silver sulfate, wherein the reaction and precipitation are performed in the presence of an aqueous soluble inorganic additive compound containing a cation capable of forming a sulfate salt that is less soluble than silver sulfate or a halide anion or an oxyanion capable of forming a silver salt that is less soluble than silver sulfate, the amount of additive being a minor molar percentage, relative to the molar amount of silver sulfate precipitated, and effective to result in precipitation of particles comprising primarily silver sulfate having a mean grain-size of less than 70 micrometers.

The present invention provides a facile and rapid method of production of substantially free flowing powders of micrometer grain-size primarily silver sulfate particles with uniform morphology and size produced by aqueous precipitation methods well adapted to large-scale commercial production.

The precipitated micron-sized particle grains are stabilized against excessive aggregation by the inorganic additive, resulting in less agglomerated aqueous dispersions and more readily dispersed dry or substantially dry powders of silver sulfate. The invention avoids or limits need for any additional and potentially complicating steps of milling, grinding and sieving that may be required to obtain equivalent-sized particle grains of silver sulfate from materials precipitated in the absence of the inorganic additives of the invention.

The materials provided by the invention also often possess good thermal stability in the form of very minor discoloration from the direct heating of the materials or heating of composites of the materials of the inventions in combination with plastics, polymers, resins, etc.; and impart antibacterial, antifungal and antiviral properties.

DETAILED DESCRIPTION OF THE INVENTION

In accordance with the process of the present invention, an aqueous solution of a soluble silver salt and an aqueous solution of a source of inorganic sulfate ion may be added together under turbulent mixing conditions in a precipitation reactor. In the absence of the invention, such a precipitation reaction has been found to typically result in substantial agglomeration (aggregation) of the precipitated primary crystallites such that the actual precipitated particle grain-sizes may be significantly larger than may be desired for some applications. In accordance with the present invention, it has been found that performing the precipitation of silver sulfate particles in the reactor in the presence of an effective minor amount of specified inorganic additives enables obtaining stable, micrometer size (e.g. less than about 70 micrometer) dispersed primarily silver sulfate particles, of a grain-size smaller than that obtained in the absence of the inorganic additive.

The specified inorganic additives employed in the present invention to refer to an aqueous soluble inorganic compound containing a cation capable of forming an insoluble sulfate salt that is less soluble than silver sulfate, or a halide anion or an oxyanion capable of forming an insoluble silver salt that is less soluble than silver sulfate. An example of the former is the strontium cation, exemplified by strontium nitrate. Examples of halide ions include chloride, bromide, and iodide, with chloride being a preferred halide ion for use in the invention. Oxyanions (alternatively spelled oxoanions) are negatively charged ions that contain oxide. Oxyanions may contain both bridging and terminal oxide groups, and may be further termed a dioxyanion, trioxyanion or polyoxyanion as the number of oxygen atoms per metal or other atom increases correspondingly. Examples of oxyanions include aluminate, borate, bromate, bromite, carbonate, chlorate, perchlorate, chlorite, hypochlorite, chromate, dichromate, iodate, hypoiodate, periodate, iodite, hypoiodite, nitrate, nitrite, hyponitrite, manganate, permanganate, phosphate, phosphite, hypophosphite, pyrophosphate, silicate, sulfate, persulfate, peroxydisulfate, sulfite, hyposulfite and tungstate. Preferred oxyanions for use in the invention include bromate, carbonate, chlorite, iodate, and tungstate anions; exemplified, for instance, by the alkali metal salts thereof. The inorganic additive compound preferably has an aqueous solubility of at least 1 g/L.

The inorganic additive compound is added to the precipitation reactor as a minor component (i.e., less than 50 molar percent), relative to the molar amount of silver, effective for obtaining stable, primarily silver sulfate particles of a mean size less than 70 microns. As demonstrated in the examples, effective amounts of additive required may depend upon the specific inorganic additive compound employed, but generally will typically be at least about 0.01 molar percent, based on the molar amount of silver reacted, although even lower concentrations may also be effective depending upon optimized precipitation reaction conditions. By restricting the amount of additive to a minor molar amount relative to the amount of silver, negative attributes associated with the inorganic character of the additive may be controlled in the resulting precipitated particles comprising primarily silver sulfate, while the minor amounts of additive may still be effective to achieve the desired precipitated particle size. In preferred embodiments of the invention, additives are selected which are effective at molar amounts less than 10 percent, more preferably less than 5 percent, and most preferably less than 1 percent, based on the molar amount of silver. In various embodiments of the invention, the inorganic compound may be added to the reactor before, during and/or after addition of the aqueous soluble silver salt solution to the reactor.

Soluble silver salts that may be employed in the process of the invention include silver nitrate, acetate, propionate, chlorate, perchlorate, fluoride, lactate, etc. Inorganic sulfate ion sources include sulfuric acid, ammonium sulfate, alkali metal (lithium, sodium, potassium, rubidium, cesium) sulfate, and alkaline earth metal (such as magnesium) sulfate, transition metal (such as zinc, cadmium, zirconium, yttrium, copper, nickel, iron) sulfate, etc. In a preferred embodiment of the invention, the soluble silver salt employed is silver nitrate and the source of inorganic sulfate ion is ammonium sulfate or sulfuric acid, more preferably ammonium sulfate.

Turbulent mixing conditions employed in precipitation reactors in accordance with the process of the invention may be obtained by means of conventional stirrers and impellers. In a specific embodiment of the invention, the reactants are preferably contacted in a highly agitated zone of a precipitation reactor. Preferred mixing apparatus, which may be used in accordance with such embodiment, includes rotary agitators of the type which have been previously disclosed for use in the photographic silver halide emulsion art for precipitating silver halide particles by reaction of simultaneously introduced silver and halide salt solution feed streams. Such rotary agitators may include, e.g., turbines, marine propellers, discs, and other mixing impellers known in the art (see, e.g., U.S. Pat. Nos. 3,415,650; 6,513,965; 6,422,736; 5,690,428; 5,334,359; 4,289,733; 5,096,690; 4,666,669; EP 1156875, WO-0160511).

While the specific configurations of the rotary agitators which may be employed in preferred embodiments of the invention may vary significantly, they preferably will each employ at least one impeller having a surface and a diameter, which impeller is effective in creating a highly agitated zone in the vicinity of the agitator. The term "highly agitated zone" describes a zone in the close proximity of the agitator within which a significant fraction of the power provided for mixing is dissipated by the material flow. Typically, it is contained within a distance of one impeller diameter from a rotary impeller surface. Introduction of a reactant feed stream into a precipitation reactor in close proximity to a rotary mixer, such that the feed stream is introduced into a relatively highly agitated zone created by the action of the rotary agitator provides for accomplishing meso-, micro-, and macro-mixing of the feed stream components to practically useful degrees. Depending on the processing fluid properties and the dynamic time scales of transfer or transformation processes associated with the particular materials employed, the rotary agitator preferably employed may be selected to optimize meso-, micro-, and macro-mixing to varying practically useful degrees.

Mixing apparatus that may be employed in one particular embodiment of the invention includes mixing devices of the type disclosed in Research Disclosure, Vol. 382, February 1996, Item 38213. In such apparatus, means are provided for introducing feed streams from a remote source by conduits that terminate close to an adjacent inlet zone of the mixing device (less than one impeller diameter from the surface of the mixer impeller). To facilitate mixing of multiple feed streams, they may be introduced in opposing direction in the vicinity of the inlet zone of the mixing device. The mixing device is vertically disposed in a reaction vessel, and attached to the end of a shaft driven at high speed by a suitable means, such as a motor. The lower end of the rotating mixing device is spaced up from the bottom of the reaction vessel, but beneath the surface of the fluid contained within the vessel. Baffles, sufficient in number to inhibit horizontal rotation of the contents of the vessel, may be located around the mixing device. Such mixing devices are also schematically depicted in U.S. Pat. Nos. 5,549,879 and 6,048,683; the disclosures of which are incorporated by reference.

Mixing apparatus that may be employed in another embodiment of the invention includes mixers that facilitate separate control of feed stream dispersion (micromixing and mesomixing) and bulk circulation in the precipitation reactor (macromixing), such as descried in U.S. Pat. No. 6,422,736, the disclosure of which is incorporated by reference. Such apparatus comprises a vertically oriented draft tube, a bottom impeller positioned in the draft tube, and a top impeller positioned in the draft tube above the first impeller and spaced there from a distance sufficient for independent operation. The bottom impeller is preferably a flat blade turbine (FBT) and is used to efficiently disperse the feed streams, which are added at the bottom of the draft tube. The top impeller is preferably a pitched blade turbine (PBT) and is used to circulate the bulk fluid through the draft tube in an upward direction providing a narrow circulation time distribution through the reaction zone. Appropriate baffling may be used. The two impellers are placed at a distance such that independent operation is obtained. This independent operation and the simplicity of its geometry are features that make this mixer well suited in the scale-up of precipitation processes. Such apparatus provides intense micromixing, that is, it provides very high power dissipation in the region of feed stream introduction.

Once formed in an aqueous precipitation process in accordance with the invention, the resulting ultra-fine silver sulfate particles may be washed, dried and collected as a white free-flowing powder. In terms of particle size metrics, the precipitation process preferably results in producing both a small primary crystallite size and a small grain-size, along with a narrow grain-size distribution.

In discussing silver sulfate particle morphology and metrology it is important to clearly understand the definitions of some elementary and widely used terms. By primary crystallite size, one refers to that size which is commonly determined by X-Ray Powder Diffraction (XRPD). A wider XRPD line width implies a smaller primary crystallite size. Quantitatively, the crystallite size (t) is calculated from the measured X-ray peak half width (B (radians)), the wavelength of the X-ray ($\lambda$), and the diffraction angle ($\theta$) using the Scherrer equation:

$$t=0.9\ \lambda/(B \cos \theta)$$

See B. D. Cullity, "Elements of X-Ray Diffraction" (1956) Addison-Wesley Publishing Company, Inc., Chapter 9.

From a structure view, a crystallite is typically composed of many unit cells, one unit cell being the most irreducible representation of the crystal structure. The primary crystallite size should not be confused with the final grain-size. The final grain-size is determined by how many of the crystallites agglomerate. Typically, the grain-size measurement, including size frequency distribution, can be determined from light scattering measurements provided, for instance, by an LA-920 analyzer available from HORIBA Instruments, Inc. (Irvine, Calif., USA). It is important to make the distinction that having a small primary crystallite size does not guarantee a small final grain-size—this must be measured separately from the XRPD spectrum. However, a large primary crystallite size will preclude a small final grain-size. Thus to fully characterize a particulate dispersion one would need a knowledge of final grain-size (e.g. HORIBA), size-frequency distribution embodied, for example, in the standard deviation (e.g. HORIBA), and primary crystallite size (XRPD).

In preferred embodiments, silver sulfate particles obtained in accordance with the invention can be combined with a melt-processed polymer (e.g. thermoplastic and thermoset) to form a composite, where the composite is defined as the silver sulfate dispersed in the polymer after thermal processing. The preferred thermoplastic polymers suitable for making composites are those polymeric compounds having good thermal stability and a range of melt index, preferably from about 0.3 to about 99. The weight ratio of silver sulfate to thermoplastic polymer in the composite may vary widely depending on application. However, it is preferred that the ratio is $\geq 0.01$: 99.99, more preferably $\geq$ about 1:99, and most preferably $\geq$ about 5:95.

A preferred method for making the composite of the silver sulfate, together with any optional addenda, in polymer is melt blending with the thermoplastic polymer using any suitable mixing device such as a single screw compounder, blender, paddle compounder such as a Brabender, spatula, press, extruder, or molder such as an injection molder. However, it is preferred to use a suitable batch mixer, continuous mixer twin-screw compounder such as a PolyLab or Leistritz, to ensure proper mixing and more uniform dispersal. Twin-screw extruders are built on a building block principle. Thus, mixing of silver sulfate, temperature, mixing rotations per minute (rpm), residence time of resin, as well as point of addition of silver sulfate can be easily changed by changing screw design, barrel design and processing parameters. Similar machines are also provided by other twin-screw compounder manufacturers like Werner and Pfleiderrer, Berstorff, and the like, which can be operated either in the co-rotating or the counter-rotating mode.

One method for making the composite is to melt polymer in a glass, metal or other suitable vessel, followed by addition of the silver sulfate salt of this invention. The polymer and silver sulfate are mixed using a spatula until the silver sulfate is uniformly dispersed in the polymer. Another method for making the composite is to melt the polymer in a small compounder, such as a Brabender compounder, followed by addition of the silver sulfate salt of this invention. The polymer and silver sulfate are mixed using the compounder until the silver sulfate is uniformly dispersed in the polymer. Alternatively, the silver sulfate of this invention can be predispersed in the polymer followed by addition of this mixture to the mixing device. Yet, in another method such as in the case of a twin-screw compounder, this compounder is provided with main feeders through which resins are fed, while silver sulfate might be fed using one of the main feeders or using the side stuffers. If the side stuffers are used to feed the silver sulfate then screw design needs to be appropriately configured. The preferred mode of addition of silver sulfate material to the thermoplastic polymer is through the use of the side stuffer, though top feeder can be used, to ensure proper viscous mixing and to ensure dispersion of the silver sulfate through the polymer matrix as well as to control the thermal history. In this mode, the thermoplastic polymer is fed using the main resin feeder, and is followed by the addition of the silver sulfate through the downstream side stuffer. Alternatively, the polymer and silver sulfate can be fed using the main feeders at the same location. In yet another embodiment the silver sulfate can be pre-dispersed in a thermoplastic polymer in a masterbatch, and further diluted in the compounder. As before, the masterbatch and the thermoplastic polymer can be fed through the main resin feeder and/or the side or top feeder, depending on specific objectives. It is preferred that the resultant composite material obtained after compounding is further processed into pellets, granules, strands, ribbons, fibers, powder, films, plaques and the like for subsequent use.

Polymers suitable to the invention include those melt-processed between about 60-500° C. A non-limiting list of such polymeric materials include:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked, known as PEX), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

2. Mixtures of the polymers mentioned above, for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Vinyl polymers and copolymers used in thermoplastics, such as poly(vinyl chloride) and derivatives thereof; polystyrene and derivatives thereof; poly(acrylic acid); polyacrylates; polycyanoacrylate; poly(alkyl acrylates) such as poly (methyl acrylate) and poly(ethyl acrylate); poly(methacrylic acid) (PMAA); poly(methyl methacrylate) (PMMA); polyacrylamide; polyacrylonitrile; polyisobutylene; polybutenes; polydicyclopentadiene; polytetrafluoroethylene (TEFLON); polytrichlorofluoroethylene; polychlorotrifluoroethylene; poly(vinyl acetate); poly(vinyl alcohol); poly(vinyl butyral) (BUTVAR™); poly(N-vinyl carbazole), poly(vinyl chloride-acetate); poly(vinyl ethers); poly(vinylidene chloride); poly (vinylidene fluoride); poly(vinyl fluoride); poly(vinyl pyrolidone); poly(vinyl pyrolidinone); allyl resins (crosslinked diallyl and triallyl esters).

5. Polyesters such as the commercially available linear polyesters, for example poly(ethylene terephthalate) (PET), poly(trimethylene terephthalate) (PIT), poly(butylene terephthalate) (PBT), poly(ethylene naphthalene-2,6-dicarboxylate) (PEN), poly(4-hydroxybenzoate), poly(bisphenol A terephthalate/isophthalate), poly(1,4-dihydroxymethylcyclohexyl terephthalate), polycarbonate (such as bisphenol A polycarbonate), polycaprolactone, poly(glycolic acid), poly (lactic acid); the bacterial polyesters known collectively as poly(hydroxy alkanoates) (PHA), such as poly(3-hydroxybutyrate) (PHB), phenyl-substituted PHA and unsaturated PHA; and the man-made random copolymer poly(3-hydroxybutyrate-co-3-hydroxyvalerate) (PHBV); the hyperbranched polyesters; the crosslinked or network polyesters commonly called alkyds or polyester resins, including i) the saturated polyester resins that utilize polyfunctional alcohols and acids, such as glycerol, pentaerythritol, sorbitol, citric acid, trimellitic acid, or pyromellitic dianhydride, to crosslink during the esterification reaction, typically used to prepare oil-modified alkylds and styrenated alkyds, and ii) the unsaturated polyester resins that utilize double bonds incorporated into the polyester backbone to crosslink in a separate addition polymerization reaction step.

6. Polyamides and polypeptides, including, for example, the commercially available commodity nylons such as Nylon 6 (polycaprolactam) and Nylon 66 [poly(hexamethylene adipamide)]; commercial specialty nylons such as Nylon 7 [poly (7-heptanamide)], Nylon 8 [polycaprolactam], Nylon 9 [poly (9-nonanamide)], Nylon 11 [poly(11-undecanamide)], Nylon 12 [polylauryllactam], Nylon 46 [poly(tetramethylene adipamide)] Nylon 69 [poly(hexamethylene azelamide)] Nylon 610 [poly(hexamethylene sebacamide)] Nylon 612 [poly(hexamethylene dodecanediamide)]; commercially available polymers poly(methylene-4,4'-dicyclohexylene dodecanediamide), poly(1,4-cyclohexylenedimethylene suberamide), poly(m-phenylene isophthalamide) (DuPont NOMEX™), poly(p-phenylene terephthalamide) (DuPont KEVLAR™), poly(2,4,4-trimethylhexamethylene terephthalamide), poly(2,2,4-trimethylhexamethylene terephthalamide); other nylons such as Nylon 1 and derivatives thereof, Nylon 3 (poly-β-alanine), Nylon 4, Nylon 5; branched nylons; wholly aromatic polyamides; aliphatic-aromatic polyamides; polyureas; polyurethane fibers, such as those used in "hard" segments of elastomeric AB block copolymers (DuPont Spandex technology), in reaction injection molding (RIM) systems for making automobile parts (e.g. bumpers), and in rigid and flexible foams (such as HYPOL™ available from W. R. Grace & Co. (USA)); polyhydrazides; polyimides, such as poly(4,4'-oxydiphenylene-pyromellitimide) (DuPont KAPTON™); polyaspartimide; polyimidesulfones; polysulfonamides; polyphosphonamides; and proteins, such as wool, silk, collagen, recombinant human collagen, gelatin and regenerated protein.

7. Other polymers used in engineering plastics, including, for example, polyethers such as poly(ethylene oxide) (PEO), poly(ethylene glycol), polytetrahydrofuran or other polyethers used, for instance, in "soft" segments of elastomeric AB block copolymers (DuPont Spandex technology), polyoxymethylene (acetal), poly(phenylene oxide) (PPO), poly(hexafluoropropylene oxide), poly[3,3-(dichloromethyl)trimethylene oxide], polytetrahydrofuran, polyetherketones (PEK), polyetherketoneketones (PEKK), polyetheretherketones (PEEK), polyetherketoneether ketoneketones (PEKEKK), polyetherimides (PEI); polyethersulfones (PES) such as VICTREX available from ICI; polysulfones (PSU) such as ASTREL™ available from 3M; polysupersulfones (PSS); polybenzimidazoles (PBI); polysulfides such as poly(p-phenylene sulfide) (PPS) and poly(alkylene polysulfides) (known as Thiokol rubbers); and thermoplastic elastomers such as polyether block amides (PEBAX™).

8. Polymers used in thermosetting plastics, laminates and adhesives, including, for example, phenol-formaldehydes (often referred to as phenolic resins), chemically modified phenolic resins optionally containing furfural, 5-hydroxymethylfurfural, acrolein, acetaldehyde, butyraldehyde, resorcinol, bisphenol A, o- or p-cresol, o- or p-chlorophenol, p-t-butylphenol, p-phenylphenol, p-n-octylphenol, unsaturated phenols derived from cashew nut shell liquid (such as cardanol), unsaturated phenols from tung oil (such as α-eleostearic acid), 2-allylphenol, naturally occurring phenols such as hydrolyzable tannins (pyrogallol, ellagic acid, glucose esters or condensed forms of gallic acid), condensed tannins (flavonoid units linked together with carbohydrates) and lignin; phosphate esterified phonolic resins; furan resins; bisphenol A-furfural resins; unsaturated polyesters; polyether epoxy resins; amino resins such as urea-formaldehydes and melamine-formaldehydes (FORMICA™ and BASOFIL™); resoles; novolacs; crosslinked novolacs (e.g. KYNOL™); epoxy cresol novolacs, and epoxy phenol novalacs.

9. Polymers and copolymers used in synthetic elastomers, including, for example, poly(acrylonitrile-butadiene); poly(styrene-butadiene) (SBR), poly(styrene-butadiene) block and star copolymers; poly(styrene-acrlyonitrile) (SAN), poly(styrene-maleic anhydride) (SMA), poly(styrene-methylmethacrylate); poly(acrylonitrile-butadiene-styrene) (ABS); poly(acrylonitrile-chlorinated polyethylene-styrene); poly(acrylonitrile-butadiene-acrylate); polybutadiene, specifically the cis-1,4 polymer; ethylene-propylene-diene-monomer (EPDM); neoprene rubbers, such as cis or trans-1,4-polychloroprene and 1,2-polychloroprene; cis or trans-1,4-polyisoprene; poly(isobutylene-isoprene); poly(isobutylene-cyclopentadiene); poly(1-octenylene)(polyoctenamer); poly(1,3-cyclo-pentenylenevinylene)(norbornene polymer).

10. Other natural polymers, including, for example, natural rubbers such as hevea (cis-1,4-polyisoprene), guayule (cis-1, 4-polyisoprene), guta percha (trans-1,4-polyisoprene), balata (trans-1,4-polyisoprene) and chicle (cis and trans-1,4-polyisoprene); lignin; humus; shellac; amber; Tall oil derived polymers (rosin); asphaltenes (bitumens); polysaccharides, such as native cellulose derived from seed hair fibers (cotton, kapok, coir), bast fibers (flax, hemp, jute, ramie) and leaf fibers (manila hemp, sisal hemp); regenerated cellulose such as viscose rayon and cellophane; derivatives of cellulose including the nitrate (e.g. CELLULOID™), acetate (fibers of which are known as cellulose rayon), propionate, methacrylate, crotonate and butylate esters of cellulose; acetate-propionate and acetate-butyrate esters of cellulose, and mixtures thereof; the methyl, ethyl, carboxymethyl, aminoethyl, mercaptoethyl, hydroxylethyl, hydroxypropyl and benzyl ether derivatives of cellulose (e.g. "thermoplastic starches"); nitrocellulose; vinyl and nonvinyl graft copolymers of cellulose (e.g. ETHYLOSE™); crosslinked cellulose; hemicelluloses (amorphous) such as xylan, mannan, araban and galactans; starch, including amylase and amylopectin; derivatives of starch such as allylstarch, hydroxyethylstarch, starch nitrate, starch acetate, vinyl graft copolymers of starch such as stryrenated starch; crosslinked starch made using, for instance, epichlorohydrin; chitin; chitosan; alginic acid polymer; carrageenin; agar; glycogen; dextran; inulin; and natural gums such as gum arabic, gum tragacanth, guar gum, xanthum gum, gellan gum and locust bean gum.

11. Heterocyclic polymers, including, for example, polypyrroles, polypyrazoles, polyfurans, polythiophenes, polycyanurates, polyphthalocyanines, polybenzoxazoles, polybenzothiazoles, polyimidazopyrrolones, poly(1,3,4-oxadiazoles) (POD), poly(1,2,4-triazoles), poly(1,3,4-thiadiazoles), polyhydantoins, poly(parabanic acids) also known as poly(1,3-imidazolidine-2,4,5-triones), polythiazolines, polyimidines, polybenzoxazinone, polybenzoxazinediones, polyisoindoloquinazolinedione, polytetraazopyrene, polyquinolines, polyanthrazolines, poly(as-triazines).

12. Other organic polymers, including, for example, polyamines such as polyanilines, Mannich-base polymers; and polyaziridines; polycarbodiimides; polyimines (also called azomethine or Schiff base polymers); polyamidines; polyisocyanides; azopolymers; polyacetylenes; poly(p-phenylene); poly (o-xylylene); poly(m-xylylene); poly(p-xylylene) and chlorinated poly(p-xylylene) (Union Carbide PARYLENE™); polyketones; Friedel-Crafts polymers; Diels-Alder polymers; aliphatic and aromatic polyanhydrides; ionens; ionene-polyether-ionene ABA block copolymers; halatopolymers; and synthetic bioabsorbable polymers, for example, polyesters/polyactones such as polymers of polyglycolic acid, glycolide, lactic acid, lactide, dioxanone, trimethylene carbonate, polyanhydrides, polyesteramides, polyortheoesters, polyphosphazenes, and copolymers of these and related polymers.

13. Inorganic polymers, including, for example, polysiloxanes, polysilanes, polyphosphazines, carborane polymers, ploycarboranesiloxanes (DEXSIL™ and UCARSIL™), poly(sulfur nitride), polymeric sulfur, polymeric selenium, polymeric tellurium, boron nitride fibers, poly(vinyl metallocenes) of ferrocene and ruthenocene, polyesters and polyamides containing metallocenes in the polymer backbone, poly(ferrocenylsilane); poly(ferrocenylethylene); organometallic vinyl polymers containing manganese, palladium or tin, and copolymers of the former with poly(methyl methacrylate), which are used in biocidal paints for marine applications such as ship hulls and off-shore drilling platforms; metal-containing polyesters and polyamides; polymeric nickel(o)-cyclooctatetraene, polymeric norbomadiene-silver nitrate; arylethynyl copper polymers; coordination polymers, such as polymers resulting from the reaction of bis(1,2-dioxime) with nickel acetate, phthalocyanine-type polymers, network transition metal polyphthalocyanines linked through imide or benzimidazole groups, cofacially linked polyphthalocyanines, ligand exchange polymers resulting from the reaction of bis(β-diketone) and metal acetylacetonates or tetrabutyl titanate, polymers resulting from the reaction of bis(8-hydroxy-5-quinolyl) derivative, and its thiol analogs, with metal acetylacetonates; polymeric chelates, such as polyamides resulting from the reaction of diacid chloride with thiopicolinamides, and vinyl polymers containing pendant crown ethers, such as poly(4'-vinylbenzo-18-crown-6).

Homopolymers, copolymers and blends of the polymers described above may have any stereostructure, including syndiotactic, isotactic, hemi-isotactic or atactic. Stereoblock polymers are also included. The polymers may be amorphous, crystalline, semicrystalline or mixtures thereof; and possess a range of melt index, preferably from about 0.3 to about 99. The polymers described above may be further derivatized or functionalized (e.g. chlorinated, brominated, fluorinated, sulfonated, chlorosulfonated, saponified, hydroborated, epoxidated) to impart other features (e.g. physical/chemical, end-group conversion, bio and photodegradation), or in preparation for subsequent crosslinking, block and graft copolymerization.

Polyolefins, preferably polyethylene and polypropylene, and vinyl polymers exemplified in the preceding paragraphs can be prepared by different, and especially by the following, methods: a) radical polymerization (normally under high pressure and at elevated temperature); b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

Polyesters for use in the invention may be manufactured by any known synthetic method, including, for example, direct esterification, transesterification, acidolysis, the reaction of alcohols with acyl chlorides or anhydrides, the reaction of carboxylic acids with epoxides or alkylhalides, and by ring-opening reactions of cyclic esters. Copolyesters, copolymers containing a polyester, and polymer blends, such as engineering plastics comprising polyblends of polycarbonate with PBT or ABS (acrylonitrile-butadiene-styrene) are specifically contemplated. Solution and interfacial (phase-transfer) methods, catalyzed low temperature and high temperature synthetic methods may be employed.

Polyamides for use in the invention can be manufactured by any known method, including, for example, solution polymerization, interfacial polymerization in which an acid chloride and a diamine are used as raw materials, by melt polymerization, solid-phase polymerization, or melt extrusion polymerization in which a dicarboxylic acid and a diamine are used as raw materials.

Besides the polymer and silver sulfate, the composite material or masterbatch can include any optional addenda. These addenda can include nucleating agents, fillers, plasticizers, surfactants, intercalates, compatibilizers, coupling agents, impact modifiers, chain extenders, colorants, lubricants, antistatic agents, pigments such as titanium oxide, zinc oxide, talc, calcium carbonate, dispersants such as fatty amides (e.g. stearamide), metallic salts of fatty acids (e.g. zinc stearate, magnesium stearate), dyes such as ultramarine blue, cobalt violet, antioxidants, fluorescent whiteners, ultraviolet absorbers, fire retardants, abrasives or roughening agents such as diatomaceous earth, cross-linking agents, foaming agents and the like. These optional addenda and their corresponding amounts can be chosen according to need. Incorporation of these optional addenda in the purge material can be accomplished by any known method.

Polymer composites of the invention may be fabricated in any known shape, such as fibers, films or blocks. Fibers may be solid or hollow, and either round or non-round in cross section. The latter may assume ribbon, wedge (triangular) and core (hub & spokes), multilobe (such as trilobe, cross, star and higher multilobe cross sections), elliptical and channeled cross sections (designed to promote moisture wicking, such as in COOLMAX™ fibers). Bicomponent and multi-component fiber configurations, such a concentric sheath/core, eccentric sheath/core, side-by-side, pie wedge, hollow pie wedge, core pie wedge, three islands and islands-in-the-sea, are specifically contemplated.

Splittable synthetic fibers, such as those spun of at least two dissimilar polymers in either segment-splittable or dissolvable "islands-in-the-sea" formats, are contemplated for use in the invention. Segment splittable fibers are typically spun with 2 to 32 segments in a round fiber, although 16 segments in a pie wedge (or "citrus") cross section and 8 segments in a hollow or core pie wedge cross section are commonly used at production scales. Microfibers of 2-4 micron diameter, typically with a wedge shaped cross section, are produced after some energy input received during subsequent textile processing (e.g. hydro-entanglement, carding, airlaying, wetlaying, needlepunching) causes the segments to separate. Segmented ribbon and segmented multilobe (e.g. segmented cross and tipped trilobe) cross sections offer enhanced fiber splittability, but the cost of spinnerets capable of forming these cross section shapes is high. Splittable segmented bicomponent fibers of nylon/polyester are commercially available (e.g. DUOTEX™ and STARFIBER™). Other polymer combinations used in splittable bicomponent fibers include polypropylene/nylon, polypropylene/polyester, polypropylene/poly(acrylonitrile), polypropylene/polyurethane, all-polyester splittable fibers made from poly(lactic acid)/PET, and all-polyolefin splittable fibers made from polypropylene/poly(methyl pentene).

Splittable fiber technology as originally disclosed in U.S. Pat. No. 3,705,226 employed an "islands-in-the-sea" format in which a staple fiber was spun with extremely fine diameter PET fibers surrounded by a dissolvable "sea" of copolymer. Suitable dissolving polymers include polystyrene (soluble in organic solvents), poly(lactic acid), polyvinyl alcohol, thermoplastic starches and other co-polyesters soluble in hot water. Nylon microfibers of about 6 micron diameter have been produced commercially from a fiber originally containing 37 islands of Nylon 6 in an alkali-soluble copolyester sea. Island/sea fibers with up to 600 islands have yielded microfibers about 1 micron in diameter.

Silver sulfate particles precipitated in accordance with the invention can be incorporated within plastics and polymers to provide antimicrobial (antibacterial and/or antifungal) or antiviral protection to the plastics and polymers in a variety of end-use applications. Typical end-use applications include, but are not limited to, extruded and non-extruded face fibers for carpets and area rugs (e.g. rugs with polypropylene face fibers (such as commercial, retail or residential carpet); carpet backing (either primary or secondary backing, comprising woven or nonwoven polypropylene fibers), or the latex adhesive backings used in carpet (commercial, residential or retail)). In addition, antimicrobial-incorporated and antiviral-incorporated polymers may also be used in liquid filtration media (such as non-woven filtration media for pools and spas, waste water treatment, potable water treatment, and industrial applications such as metalworking); non-woven air filtration media (such as commercial and residential furnace, HVAC or humidity control filters, air purifiers, and HEPA filters, and cabin air filters for automobiles and airplanes). Further, antimicrobial-incorporated polymers can be used for outdoor fabrics (such as woven and non-woven car and boat covers, tarps, tents, canvas, sails, ropes, pool covers, patio upholstery (such as umbrellas, awnings, seating), camping gear and geotextiles), building materials (such as drywall, weather stripping, insulation, housewrap and roof wrap, wall paper, flooring materials such as cement, concrete, mortar and tile, synthetic marble for kitchen and bath counters and sinks, sanitary ceramics, toilets, shower stalls and curtains, sealing materials (such as paints, adhesives for plumbing and packaging, glazing for windows, tile and vitreous china, grout), push buttons for elevators, handrails for stairs, mats, and knobs), industrial equipment (such as tape, tubing, barrier fabrics, conveyor belts, insulators and insulation for wire and cable, plumbing supplies and fixtures, gaskets, collection and storage equipment (including piping systems, silos, tanks and processing vessels) and coatings used on the inside of fire system sprinkler pipes), daily necessities (such as chopping boards, disposable gloves, bowls, kitchen drain baskets, kitchen refuse baskets, kitchen knife handles, chopsticks, tableware, table cloths, napkins, trays, containers, lunch boxes, chopstick cases, dusters, sponges, brooms, mops, wipes, bathroom stools, washbowls, pales, cupboards, soap cases, shampoo holders, toothbrush holders, toothbrushes, dental floss, razor blade handles, wrapping films, food wraps and packaging, canteens, emergency water tanks, toilet seats, hairbrushes, combs, scrubbers, tools and tool handles, cosmetics and cosmetic containers, and clothing). Other uses envisioned include incorporation the materials of the invention into stationary and writing materials (such as mechanical pencils, ball-point pens, pencils, erasers, floppy disk cases, clipboards, clear paper holders, fancy cases, video tape cases, photo-magnetic disk shells, compact disk cases, desk mats, binders, book covers, writing paper and pocket books), automobile parts (such as a steering wheels, armrests, panels, shift knobs, switches, keys, door knobs, assist grips), appliances (such as refrigerators, washing machines, vacuum cleaners and bags, air conditioners, clothing irons, humidifiers, dehumidifiers, water cleaners, dish washers and dryers, rice cookers, stationary and mobile telephones, copiers, touch panels for ATM or retail kiosks (e.g. photo-kiosks, etc.)), textile products (such as socks, pantyhose, undergarments, inner liners for jackets, gloves and helmets, towels, bathing suits, toilet covers, curtains, carpet fibers, pillows, sheets, bedclothes, mattress ticking, sleeping bags, nose and mouth masks, towels, caps, hats, wigs, etc.) goods related to public transportation (such as overhead straps, handles and grips, levers, seats, seat belts, luggage and storage racks) sporting goods (such as balls, nets, pucks, whistles, mouth pieces, racket handles, performance clothing, protective gear, helmets, indoor and outdoor artificial turf, shoe linings and reinforcements, tools, structures and ceremonial objects used in athletic events and the martial arts), medical applications (such as bandages, gauze, catheters, artificial limbs, implants, instruments, scrubs, facemasks, shields, reusable and disposable diapers, sanitary napkins, tampons, condoms, uniforms, gowns and other hospital garments requiring aggressive and harsh cleaning treatments to allow the garment to be safely worm by more than one person). Miscellaneous applications for the invention further involve inclusion in musical instruments (such as in reeds, strings and mouthpieces), contact lens, lens keepers and holders, plastic credit/debit cards, sand-like materials for play boxes, cat and pet litter, jewelry and wrist watch bands.

Application of the antimicrobial agents of the invention for medical uses is specifically contemplated, and formulations may be incorporated in a variety of formats:

1. Coatings of the antimicrobial agent on medical grade substrates, for example, dressings, packings, meshes, films, filtering surfaces, filters, infusers, fibers such as dental floss or sutures, containers or vials, from materials composed of, for example, polyethylene, high density polyethylene, polyvinylchloride, latex, silicone, cotton, rayon, polyester, nylon, cellulose, acetate, carboxymethylcellulose, alginate, chitin, chitosan and hydrofibers;
2. Powders (i.e. as free standing powders) of the antimicrobial agent, or as coatings of the antimicrobial agent on biocompatible substrates in powder form, preferably on hydrocolloids, bioabsorbable and/or hygroscopic substrates such as:
    Synthetic Bioabsorbable Polymers: for example, polyesters/polyactones such as polymers of polyglycolic acid, glycolide, lactic acid, lactide, dioxanone, trimethylene carbonate, polyanhydrides, polyesteramides, polyortheoesters, polyphosphazenes, and copolymers of these and related polymers or monomers, or
    Naturally Derived Polymers:
        Proteins: albumin, fibrin, collagen, elastin;
        Polysaccharides: chitosan, alginates, hyaluronic acid; and
        Biosynthetic Polyesters: 3-hydroxybutyrate polymers;
3. Occlusions or hydrated dressings, in which the dressing is impregnated with a powder or solution of the antimicrobial agent, or is used with a topical formulation of the antimicrobial agent, with such dressings for example as hydrocolloids, hydrogels, polyethylene, polyurethane, polvinylidine, siloxane or silicone dressings;
4. Gels, formulated with powders or solutions of the antimicrobial agent with such materials as hydrocolloid powders such as carboxymethylcellulose, alginate, chitin, chitosan and hydrofibers, together with such ingredients as preservatives, pectin and viscosity enhancers;
5. Creams, lotions, pastes, foams and ointments formulated with powders or solutions of the antimicrobial agent, for example as emulsions or with drying emollients;
6. Liquids, formulated as solutions, dispersions, or suspensions, by dissolving coatings or powders of the antimicrobial agent, for example as topical solutions, aerosols, mists, sprays, drops, infusions and instillation solutions for body cavities and tubes such as the bladder, prostate, perintheal, pericharcliar, pleural, intestinal and ailimentary canal;

7. Formulations suitable for administration to the nasal membranes, the oral cavity or to the gastrointestinal tract, formulated with powders or liquids of the antimicrobial or noble metal in such forms as lozenges, toothpastes, gels, powders, coated dental implants, dental floss or tape, chewing gum, wafers, mouth washes or rinses, drops, sprays, elixirs, syrups, tablets, or capsules;

8. Formulations suitable for vaginal or rectal administration formulated with powders or liquids of the antimicrobial agent in such forms as suppositories, dressings, packings, tampons, creams, gels, ointments, pastes, foams, sprays, and solutions for retention enemas or instillations.

Some specific medical end-use applications in which the invention is contemplated for use include, for example:

1. Absorbing and non-absorbing suture materials, formed as monofilament or as braided or twisted multifilaments, employing materials such as silk, polyester, nylon, polypropylene, polyvinylidenefluoride, linen, steel wire, catgut (beef serosa or ovine submucosa), polyglycolactide, polyamide (e.g. polyamide nylon), fibroin, polyglycolic acid and copolymers thereof, such as, for example, a polyglycolide (or polyglycolic acid)/polycaprolactone co-polymer or a polyglycolic acid/polycaprolactam co-polymer);

2. Surgical adhesives and sealants, including, for example, cyanoacrylates, such as butyl-4-cyanoacrylate and the polymer 2-octyl cyanoacrylate (DERMABOND™); polyethylene glycol hydrogels, such as COSEAL™ (Baxter Healthcare Corporation (USA)) and DuraSeal Dural (Confluent Surgical, (USA)), purified bovine serum albumin (BSA) and glutaraldehyde, such as BIOGLUE™ (Cryolife, Inc.(USA)); fibrins, such as CROSSEAL™ (Ethicon, Inc.(USA)) and TISSEAL™; microfibrillar collagens, such as AVITENE™ flour, ENDOAVITENE™ preloaded applications, and SYRINGEAVITENE™ (Davol, Inc.(USA)); resorbable collagens, such as BIOBLANKET™ (Kensey Nash (USA)); recombinant human collagens; phase inverted biopolymers, such as POLIPHASE™ (Avalon Medical, Ltd.); fibrinogen and thrombin, such as HEMASEEL™ APR (Haemacure Corporation (Canada)), and FIBRX™ (Cryolife, Inc.(USA)); autologous processed plasma, such as ATELES™, CEBUS™, and PROTEUS™ (PlasmaSeal (USA)); polyethylene and polyurethane adhesive foams, such as those from Scapa Medical; rubber-based medical adhesives (Scapa Medical); aesthetic injectable adhesives, such as BIOHESIVE™ (Bone Solutions, Inc (USA); and others, including BAND-AID® Brand Liquid Bandage Skin Crack Gel, THOREX™ from Surgical Sealants, Inc. (USA); and "aliphatic polyester macromers" as disclosed in US20060253094;

3. Primary wound dressings, for example, TEGADERM™ Ag Mesh, TEGADERM™ Ag Mesh With Silver, TEGADERM™ HI and HG Alginate Dressings, TEGADERM™ Hydrogel Wound Filler, TEGADERM™ Foam Adhesive and Non-Adhesive Dressings, COBAN™ Self-Adherent Wrap, CAVILON™ No-Sting Barrier Film, available from 3M (USA);

4. Surgical closure tape, such as STERI-STRIP™ S Surgical Skin Closure Tape and MEDIPORE™ H Soft Cloth Surgical Tape from 3M (USA);

5. Hemostats, in the form of topical applications, such as various forms of thrombin; matrix applications, such as bovine thrombin with cross-linked gelatin granules (FLOSEAL™ from Baxter International); sheets, such as AVITENE™ microfibrillar collagen from Davol, Inc. (USA); gauze, such as BLOODSTOP™ and BLOODSTOP™ iX (LifesciencePlus (USA)), and ActCel (ActSys Medical (USA)); gelatin sponge, such as GELFOAM™; collagen sponge, such as ULTRAFOAM™ (Davol, Inc. (USA)); lyophilized collagen sponge, such as INSTAT™ (Ethicon, Inc. (USA)); and oxidized regenerated cellulose, such as OXYCEL™ and SURGICEL™ (Ethicon, Inc. (USA))

6. Dental pit and fissure sealants, and luting cements.

Application of the materials of this invention in polymer-wood composites is also contemplated. With the rising cost of wood and the shortage of mature trees, there is a need to find good quality substitutes for wood that are more durable and longer-lasting (less susceptible to termite destruction and wood rot). Over the past several years, a growing market has emerged for the use of polymer-wood composites to replace traditional solid wood products in end-use applications such as extruded and foam-filled extruded building and construction materials (such as window frames, exterior cladding, exterior siding, door frames, ducting, roof shingles and related roofline products, and exterior boardwalks and walkways); interiors and internal finishes (for example, interior paneling, decorative profiles, office furniture, kitchen cabinets, shelving, worktops, blinds and shutters, skirting boards, and interior railings); automotive (including door and head liners, ducting, interior panels, dashboards, rear shelves, trunk floors, and spare tire covers); garden and outdoor products (such as decking, fence posts and fencing, rails and railings, garden furniture, sheds and shelters, park benches, playground equipment, and playground surfaces); and finally, industrial applications (including industrial flooring, railings, marine pilings, marine bulkheads, fishing nets, railroad ties, pallets, etc.). Polymer-wood composites also offer anti-sap-stain protection.

Polymer-wood composites may vary widely in composition, with polymer content typically ranging from about 3-80% by weight depending on end-use. Injection molded products require adequate flow of the molten material; and therefore, preferably contain from about 65 to 80% by weight of the polymer component. Whereas composites requiring structural strength may typically contain only about 3-20% polymer by weight, the polymer typically serving primarily as an adhesive. Perhaps the most commonly employed polymer components are the polyolefins (polyethylene or polypropylene, high density and low density versions and mixtures thereof), although polybutene, polystyrene, and other polymers with melting temperatures between about 130°-200° C. are also used. In principal, any polymer with a melt temperature below the decomposition temperature of the cellulosic fiber component may be employed. Crosslinking chemicals (such as peroxides and vinylsilanes), compatibilizers and coupling agents (such as grafted-maleic anhydride polymers or copolymers) that incorporate functionality capable of forming covalent bonds within or between the polymer and cellulosic components may be included. Cellulosic materials can be obtained from a wide variety of sources: wood and wood products, such as wood pulp fibers; non-woody paper-making fibers from cotton; straws and grasses, such as rice and esparto; canes and reeds, such as bagasse; bamboos; stalks with bast fibers, such as jute, flax, kenaf, linen and ramie; and leaf fibers, such as abaca and sisal; paper or polymer-coated paper including recycled paper and polymer-coated paper. One or more cellulosic materials can be used. More commonly, the cellulosic material used is from a wood source. Suitable wood sources include softwood sources such as pines, spruces, and firs, and hardwood sources such as oaks, maples, eucalyptuses, poplars, beeches, and aspens. The form of the cellulosic materials from wood sources can be sawdust, wood chips, wood flour, or the like. Still, microbes such as bacteria and fungus can feed on plasticizers or other additives and environmental foodstuffs found in or on the polymer component, resulting in discoloration and structural (chemical or mechanical) degradation. The present invention provides a means to more effectively address these issues by incorporating antimicrobial or antiviral agents in either or both of the polymer and wood components of these composites.

Another emerging application to which the present invention is particularly applicable is antimicrobial nonwoven fabrics, textiles that are neither woven nor knit. Nonwoven fabric is typically manufactured by putting small fibers together in the form of a sheet or web, and then binding them either mechanically (as in the case of felt, by interlocking them with serrated needles such that the inter-fiber friction results in a stronger fabric), with an adhesive, or thermally (by applying binder (in the form of powder, paste, or polymer melt) and melting the binder onto the web by increasing the temperature, or by thermal spot bonding). Nonwovens are often classified as either durable or single-use (disposable), depending on the end-use application.

Staple nonwovens are made in two steps. Fibers are first spun, cut to a few centimeters length, and put into bales. These bales are then dispersed on a conveyor belt, and the fibers are spread in a uniform web by a wetlaid process or by carding. Wetlaid operations typically use ¼" to ¾" long fibers, but sometimes longer if the fiber is stiff or thick. Carding operations typically use ~1.5" long fibers. Fiberglass may be wetlaid into mats for use in roofing and shingles. Synthetic fiber blends are wetlaid along with cellulose for single-use fabrics. Staple nonwovens are bonded throughout the web by resin saturation or overall thermal bonding or in a distinct pattern via resin printing or thermal spot bonding. Coforming with staple fibers usually refers to a combination with meltblown, often used in high-end textile insulations.

Spunlaid nonwovens are made in one continuous process. Fibers are spun and then directly dispersed into a web by deflectors or directed with air streams. This technique leads to faster belt speeds, and lower cost. Several variants of this concept are commercially available, a leading technology is the Reicofil machinery, manufactured by Reifenhäuser (Germany). In addition, spunbond has been combined with meltblown nonwovens, coforming them into a layered product called SMS (spun-melt-spun). Meltblown nonwovens have extremely fine fiber diameters but are not strong fabrics. SMS fabrics, made completely from polypropylene are water-repellent and fine enough to serve as disposable fabrics. Meltblown nonwovens are often used as filter media, being able to capture very fine particles.

In other processes, nonwovens may start from films and fibrillate, serrate or vacuum-formed shapes made with patterned holes. The spunlace process achieves mechanical intertwining of the nonwoven fibers by the use water jets (hydro-entanglement). Ultrasonic pattern bonding is often used in high-loft or fabric insulation/quilts/bedding. In an unusual process, nonwoven housewrap (e.g. DuPont TYVEK™) utilizes polyethylene fibrils in a Freon-like fluid, forming and calendering them into a paper-like product; while spunbound polypropylene (e.g. DuPont TYPAR™) is used in carpet backing, packaging, construction (roof and housewrap) and geotextile applications.

Fiberglass nonwovens are of two basic types. Wet laid mat or "glass tissue" use wet-chopped, heavy denier fibers in the 6 to 20 micrometer diameter range. Flame attenuated mats or "batts" use discontinuous fine denier fibers in the 0.1 to 6 micron range. The latter is similar, though run at much higher temperatures, to meltblown thermoplastic nonwovens. Wet laid mat is almost always wet resin bonded with a curtain coater, whereas batts are usually spray bonded with wet or dry resin.

The use of natural fibers such as cellulose in nonwovens (e.g. nonwoven cotton mesh gauze available as TEGADERM™, and nonwoven rayon available as BEMLIESE™) has largely given way to man-made fibers such as the polyolefins and polyester (mostly PET). PET-based nonwovens are superior in resiliency, wrinkle recovery and comfort when in contact with the skin, as well as in high temperature performance. Applications for polyester (as well as polyethylene and polypropylene) nonwovens include medical (such as isolation caps, gowns, covers and masks; surgical drapes, gowns and scrub suits) hygiene (baby diapers, feminine hygiene, adult incontinence products, wipes, bandages and wound dressings), filters (gasoline, oil and air—including HEPA filtration, water, pool and spa, coffee and tea bags) geotextiles (soil stabilizers and roadway underlayment, agricultural mulch, pond and canal barriers, and sand filtration barriers for drainage tiles) technical (ceiling tile facings, circuit board reinforcement, electrical insulation, insulation backing, honeycomb structural components, roll roofing and shingle reinforcement, wall coverings, vinyl flooring reinforcement and plastic surface reinforcement (veils)) and miscelaneous (carpet backing, marine sail and tabletop laminates, backing/stabilizer for machine embroidery, filberglass batting insulation, pillows, cushions and upholstery padding, and batting in quilts or comforters).). Commercial offerings useful for wound dressings include, for example, perforated, non-adherent non-woven meshes such as; DELNET™ P530, which is a non-woven veil formed of high density polyethylene using extrusion, embossing and orientation processes, produced by Applied Extrusion Technologies, Inc. of Middletown, Del., USA. This same product is available as Exu-Dry CONFORMANT 2™ wound veil, from Frass Survival Systems. Inc., Bronx, N.Y., USA as a subset of that company's Wound Dressing Roll (Non-Adherent) products. Other useful non-woven meshes include CARELLE™ available from Carolina Formed Fabrics Corp., USA, and N-TERFACE™ available from Winfield Laboratories, Inc., of Richardson, Tex., USA.

Nylon is also excellent in high temperature applications, but its use in nonwovens is more limited due to its high cost relative to rayon, polyolefins and polyesters; and reduced comfort relative to polyesters when used as a textile. Nonetheless, nylon is used as a blending fiber in athletic wear, nonwoven garment linings and in wipes because it imparts excellent tear strength(commercial offerings include, for example, NYLON 90™ available from Carolina Formed Fabrics Corporation (USA)). Nylon is often used in surface conditioning abrasives wherein abrasive grains are adhered with resin to the internal fiber surfaces of a nonwoven nylon backing/support. Tools containing such an abrasive/nylon system take the form of nonwoven pads, nonwoven wheels, nonwoven sheets & rolls, surface conditioning discs, convolute wheels, unified or unitized wheels and flap nonwoven wheels. Nonwoven nylon is also used as an electrode separator in Ni/H and Ni/Cd batteries. An unusual specialty spunbond nylon (CEREX™) is self-bonded by a gas-phase acidification process.

Nonwoven substrates composed of multiple fiber types, including both natural and synthetic fiber materials, may be used in the present invention. Commercial offerings of such blended nonwoven layer materials have included SONTARA® 8868, a hydro-entangled material, containing about 50/50 cellulose/polyester, and SONTARA™ 8411, a 70/30 rayon/polyester blend commercially available from Dupont Canada, Mississauga, Ontario, Canada; HFE-40-047, an apertured hydro-entangled material containing about 50% rayon and 50% polyester; and NOVENET® 149-191, a thermo-bonded grid patterned material containing about 69% rayon, about 25% polypropylene, and about 6% cotton, both of the latter from Veratec, Inc., Walpole, Mass. (USA); and KEYBAK® 951V, a dry formed apertured material, containing about 75% rayon and about 25% acrylic fibers from Chicopee Corporation, New Brunswick, N.J. (USA).

In contrast to staple nonwoven fabrics that that employ short fibers of only a few centimeters in length, continuous filament nonwoven fabrics are formed by supplying a low viscosity molten polymer that is then extruded under pressure through a large number of micro-orifices in a plate known as a spinneret or die, which creates a plurality of continuous polymeric filaments. The filaments are then quenched and drawn, and collected to form a nonwoven web. Extrusion of melt polymers through micro-orifices requires that polymer additives have particle sizes significantly smaller than the orifice diameter. It is preferred that the additive particles be less than a quarter of the diameter of the orifice holes to avoid process instabilities such as filament breakage and entanglement, or "roping", of filaments while still in the molten state. Microfilaments may typically be on the order of about 20 microns in diameter, while super microfilaments may be on the order of 3-5 microns or less. Continuous filament nonwoven fabrics formed from super microfilaments are mainly used in air filters, as well as in artificial leathers and wipes. Commercial processes are well known in the art for producing continuous microfilament nonwoven fabrics of many polymers (e.g. polyethylene, polypropylene, polyester, rayon, polyvinyl acetate, acrylics, nylon). Splittable microfibers of 2-3 micron or less diameter are readily processable on nonwoven textile equipment (carded, airlaid, wetlaid, needlepunch and hydro-entanglement). As demonstrated in the examples below, the present invention enables production of stable silver sulfate particles having mean grain-sizes of less than 70 micrometers, and accordingly, may then be more efficiently incorporated into fine diameter monofilaments.

The following examples are intended to demonstrate, but not to limit, the invention.

EXAMPLES

Example 1

Comparative, No Additive

A six-liter stainless steel sponge kettle was charged with 2 L of distilled water and the temperature controlled at 40° C. A planar mixing device previously described (Research Disclosure 38213, February 1996 pp 111-114 "Mixer for Improved Control Over Reaction Environment") operating at 3000 rpm was used to ensure the homogeneity of the reactor contents. To this reactor 71.2 mL of a 3.6M solution of ammonium sulfate was added. Peristaltic pumps were used to simultaneously deliver a 640 mL solution containing 3.1M silver nitrate at a rate of 225.0 mL/min and a 333 mL solution containing 2.9M ammonium sulfate at a rate of 117.1 mL/min causing precipitation of a white product. The reaction was held at 40° C. for 5 min. The final product was washed to a conductivity of <10 mS and a portion was dried at ambient temperature. Powder X-ray diffraction confirmed the product was single-phase silver sulfate using the Powder Diffraction File reference PDF27-1403 (International Centre for Diffraction Data, 12 Campus Boulevard, Newtown Square, Pa., USA). The mean grain-size was determined by light scattering (HORIBA) to be 76 μm. Optical micrographs of dried product indicated a mean grain-size consistent with that found from the light scattering measurement.

Example 2

Comparative, Sodium Thiocyanate (1 g)

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 1 g of dissolved sodium thiocyanate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 85 μm. Optical micrographs of dried product indicated a mean grain-size consistent with that found from the light scattering measurement.

Example 3

Comparative, Sodium Chlorate (1 g) Added With Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640mL solution containing 3.1M silver nitrate at a rate of 225.0 mL/min, a 333 mL solution containing 2.9M ammonium sulfate at a rate of 117.1 mL/min and a 67 mL solution containing 1 g of dissolved sodium chlorate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 77 μm. Optical micrographs of dried product indicated a mean grain-size consistent with that found from the light scattering measurement.

Example 4

Inventive, Potassium Iodate (0.25 g) Added with Silver

A six-liter stainless steel sponge kettle was charged with 2 L of distilled water and the temperature controlled at 40° C. The reactor contents were mixed as described in Example 1.

To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 0.25 g of dissolved potassium iodate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 68 µm. Optical micrographs of dried product indicated a mean grain-size consistent with that found from the light scattering measurement.

Example 5

Inventive, Potassium Iodate (1 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 1 g of dissolved potassium iodate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 39 µm. Optical micrographs of dried product indicated a mean grain-size consistent with that found from the light scattering measurement.

Example 6

Inventive, Potassium Iodate (3 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 3 g of dissolved potassium iodate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 35 µm. Optical micrographs of dried product indicated a mean grain-size consistent with that found from the light scattering measurement.

Example 7

Inventive, Potassium Iodate (2 g) Added Before Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate and 67 mL of a solution containing 2 g of dissolved potassium iodate were added. Peristaltic pumps were used to simultaneously deliver a 640 mL solution containing 3.1M silver nitrate at a rate of 225.0 mL/min and a 333 mL solution containing 2.9M ammonium sulfate at a rate of 117.1 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 49 µm. Optical micrographs of dried product indicated a mean grain-size consistent with that found from the light scattering measurement.

Example 8

Inventive, Potassium Iodate (2 g) Added After Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min and a 333 mL solution containing 2.9M ammonium sulfate at a rate of 117.1 mL/min causing precipitation of a white product. Following a 5 min hold, a 67 mL solution containing 1 g of dissolved potassium iodate was added at a rate of 23.3 mL/min. The reaction was held at 40° C. for 5 min. The final product was washed to a conductivity of <10 mS and a portion was dried at ambient temperature. The mean grain-size was determined by light scattering (HORIBA) to be 46 µm. Optical micrographs of dried product indicated a mean grain-size consistent with that found from the light scattering measurement.

Example 9

Inventive, Sodium Bromate (1 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 1 g of dissolved sodium bromate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 61 µm. Optical micrographs of dried product indicated a mean grain-size consistent with that found from the light scattering measurement.

Example 10

Comparative, Sodium Bromate (5 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 5 g of dissolved sodium bromate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 85 μm. Optical micrographs of dried product indicated a mean grain-size consistent with that found from the light scattering measurement.

Example 11

Inventive, Sodium Chlorite (1 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 1 g of dissolved sodium chlorite at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 68 μm. Optical micrographs of dried product indicated a mean grain-size consistent with that found from the light scattering measurement.

Example 12

Inventive, Sodium Chlorite (6 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 6 g of dissolved sodium chlorite at a rate of 23.3 mL/min causing precipitation of a white product. The reaction was held at 40° C for 5 min. The final product was washed to a conductivity of <10 mS and a portion was dried at ambient temperature. The mean grain-size was determined by light scattering (HORIBA) to be 52 μm. Optical micrographs of dried product indicated a mean grain-size consistent with that found from the light scattering measurement.

Example 13

Inventive, Sodium Tungstate (2 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 2 g of dissolved sodium tungstate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 45 μm. Optical micrographs of dried product indicated a mean grain-size consistent with that found from the light scattering measurement.

Example 14

Inventive, Sodium Chloride (1 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 1 g of dissolved sodium chloride at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 41 μm. Optical micrographs of dried product indicated a mean grain-size consistent with that found from the light scattering measurement.

Example 15

Inventive, Strontium Nitrate (2 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 2 g of dissolved strontium nitrate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 61 μm. Optical micrographs of dried product indicated a mean grain-size consistent with that found from the light scattering measurement.

Example 16

Inventive, Potassium Carbonate (2 g) Added with Silver

A six-liter stainless steel sponge kettle was charged with 2 L of distilled water and the temperature controlled at 40° C. The reactor contents were mixed as described in Example 1. To this reactor 71.2 mL of a 3.6M solution of ammonium sulfate was added. Peristaltic pumps were used to simultaneously deliver a 640 mL solution containing 3.1M silver nitrate at a rate of 225.0 mL/min, a 333 mL solution containing 2.9M ammonium sulfate at a rate of 117.1 mL/min and a 67 mL solution containing 2 g of dissolved potassium carbonate at a rate of 23.3 mL/min causing precipitation of a white product. The reaction was held at 40° C. for 5 min. The final product was washed to a conductivity of <10 mS and a portion was dried at ambient temperature. The mean grain-size was determined by light scattering (HORIBA) to be 65 μm. Optical micrographs of dried product indicated a mean grain-size consistent with that found from the light scattering measurement.

Particle size measurements were performed on equilibrated aqueous dispersions of the particles as described above using a Horiba LS-920 Analyzer. The particle size characterizations of the silver sulfate materials precipitated in Examples 1-16 are summarized in Table 1 below. The amount of the additive is expressed as a weight in grams and as a molar percent relative to the moles of silver added to the reactor.

sium iodate is also effective when added just before, or shortly after the addition of the soluble silver ion. Comparison of Examples 9-10 to Example 1 indicates that sodium bromate is effective in reducing the mean grain-size of silver sulfate when added at a lower amount (0.33 molar percent), but effective only in reducing the grain-size distribution (Standard Deviation) when added at a much higher amount (1.66 molar percent). Examples 11-14 indicate that while sodium chlorite, sodium tungstate and sodium chloride are effective as additives to reduce the mean grain-size of silver sulfate, these additives are less preferred as they reduce the thermal or photo stability. Examples 15-16 indicate that potassium carbonate and strontium nitrate are likewise effective as additives in reducing the grain-size of silver sulfate.

Comparison of the mean grain-size distribution (Standard Deviation) results shown in Table 1 above indicates that for each inventive example (Examples 4-16) a reduction (i.e. a more uniform grain-size) is afforded. In contrast, the grain-size distribution is not significantly impacted when an inorganic additive not of the invention (Examples 2-3) is

TABLE 1

| Ex. No. | Additive | Additive Addition | Amount (g) | Mol % | Mean Size (μm) | Standard Deviation (μm) | Additive Silver Solubility (g/100 mL)$^e$ | Additive Sulfate Solubility (g/100 mL)$^f$ | Example Type |
|---|---|---|---|---|---|---|---|---|---|
| 1 | None | — | — | — | 76.5 | 45.2 | — | — | Comp. |
| 2 | NaSCN | with silver | 1 | 0.62 | 84.7 | 45.3 | $1.4 \times 10^{-5}$ | 7.7 | Comp. |
| 3 | NaClO3 | with silver | 1 | 0.47 | 76.8 | 44.6 | 8.6 | 7.7 | Comp. |
| 4 | KIO3 | with silver | 0.25 | 0.06 | 68.2 | 33.9 | 0.011 | 6.0 | Inv. |
| 5 | KIO3 | with silver | 1 | 0.23 | 39.4 | 31.2 | 0.011 | 6.0 | Inv. |
| 6 | KIO3 | with silver | 3 | 0.70 | 34.9 | 33.5 | 0.011 | 6.0 | Inv. |
| 7 | KIO3 | before silver | 2 | 0.47 | 48.7 | 42.4 | 0.011 | 6.0 | Inv. |
| 8 | KIO3 | after silver | 1 | 0.23 | 46.0 | 29.7 | 0.011 | 6.0 | Inv. |
| 9 | NaBrO3 | with silver | 1 | 0.33 | 60.8 | 28.6 | 0.090 | 7.7 | Inv. |
| 10 | NaBrO3 | with silver | 5 | 1.66 | 84.7 | 37.7 | 0.090 | 7.7 | Inv. |
| 11 | NaClO2 | with silver | 1 | 0.55 | 68.2$^a$ | 41.5 | 0.28 | 7.7 | Inv. |
| 12 | NaClO2 | with silver | 6 | 3.32 | 52.0$^b$ | 36.0 | 0.28 | 7.7 | Inv. |
| 13 | Na2WO4 | with silver | 2 | 0.34 | 45.2$^c$ | 31.0 | 0.0070 | 7.7 | Inv. |
| 14 | NaCl | with silver | 1 | 0.86 | 41.2$^d$ | 23.8 | $6.7 \times 10^{-5}$ | 7.7 | Inv. |
| 15 | K2CO3 | with silver | 2 | 0.72 | 65.2 | 30.1 | 0.0025 | 6.0 | Inv. |
| 16 | Sr(NO3)2 | with silver | 2 | 0.47 | 60.6 | 32.1 | 37.4 | 0.0073 | Inv. |

$^a$Product turned gray with overnight drying
$^b$Product turned gray with overnight drying
$^c$Product turned yellow with 70 C drying
$^d$Product turned gray during drying (photosensitive)
$^e$Silver solubility of silver sulfate is 0.55 g/100 mL
$^f$Sulfate solubility of silver sulfate is 0.25 g/100 mL Comparison of the mean grain-size results shown above for Examples 2-3 indicates that addition of sodium thiocyanate at 0.62 molar percent and sodium chlorate at 0.47 molar percent, respectively, are ineffective in reducing the mean grain-size of silver sulfate relative to the no additive comparison of Example 1. In contrast, Examples 4-6 indicate that potassium iodate is quite effective in reducing the mean grain-size of silver sulfate, being substantially effective at an amount as low as 0.06 molar percent. Examples 7-8 indicate that potasemployed. In addition, examination of the corresponding silver and sulfate complex solubilities for the additives given in Table 1, indicates that the inorganic additives of the invention are those that possess either a cation capable of forming an insoluble sulfate salt that is less soluble than silver sulfate, or a halide anion or an oxyanion capable of forming an insoluble silver salt that is less soluble than silver sulfate.

It is specifically contemplated to prepare plastic, polymer and polymer-wood composites containing silver sulfate prepared with the inorganic additives of the invention for the purpose of imparting antimicrobial (e.g. antibacterial, antifungal, antimold, antiyeast, antialgae) and antiviral properties. Further testing of polymer composites comprising primarily silver sulfate particles prepared in accordance with the invention has been performed to confirm antimicrobial properties thereof.

The invention has been described in detail with particular reference to certain preferred embodiments thereof, but it will be understood that variations and modifications can be effected within the spirit and scope of the invention.

The invention claimed is:

1. A process comprising reacting an aqueous soluble silver salt and an aqueous soluble source of inorganic sulfate ion in an agitated precipitation reactor vessel and precipitating particles comprising primarily silver sulfate, wherein the reaction and precipitation are performed in the presence of an aqueous soluble inorganic additive compound containing a cation capable of forming a sulfate salt that is less soluble than silver sulfate or a halide anion or an oxyanion capable of forming a silver salt that is less soluble than silver sulfate, the amount of additive being a minor molar percentage, relative to the molar amount of silver sulfate precipitated, and effective to result in precipitation of particles comprising primarily silver sulfate having a mean grain-size of less than 70 micrometers, wherein the inorganic additive compound comprises an iodate salt.

2. A process according to claim 1, wherein the amount of the inorganic additive present during the precipitation is less than 10 molar percent, relative to the molar amount of silver sulfate precipitated.

3. A process according to claim 1, wherein the amount of the inorganic additive present during the precipitation is less than 5 molar percent, relative to the molar amount of silver sulfate precipitated.

4. A process according to claim 1, wherein the amount of the inorganic additive present during the precipitation is at least 0.06 molar percent, relative to the molar amount of silver sulfate precipitated.

5. A process according to claim 1, wherein the amount of additive present during the precipitation is at least 0.01 molar percent, relative to the molar amount of silver sulfate precipitated.

6. A process according to claim 1, wherein the inorganic additive compound comprises potassium iodate.

7. A process according to claim 1, wherein the inorganic additive compound has an aqueous solubility of at least 1 g/L.

8. A process according to claim 1, wherein the soluble silver salt comprises silver nitrate, and the soluble source of inorganic sulfate ion comprises ammonium sulfate.

9. A process according to claim 1, wherein a portion of the solution of the soluble source of inorganic sulfate ion is added simultaneously with the solution of the soluble silver salt.

* * * * *